United States Patent [19]

Hauck et al.

[11] 4,127,579
[45] Nov. 28, 1978

[54] SUBSTITUTED PIPERIDINYLPROPANOLS

[75] Inventors: Frederic P. Hauck, Bridgewater; Rita T. Fox, Princeton; John R. Watrous, Pennington, all of N.J.

[73] Assignee: E. R. Squibb & Sons, Inc., Princeton, N.J.

[21] Appl. No.: 855,038

[22] Filed: Nov. 25, 1977

[51] Int. Cl.² .................. C07D 295/10; C07D 413/04; C07D 401/04
[52] U.S. Cl. .................................... 546/17; 424/267; 546/198; 546/199; 546/206
[58] Field of Search .................... 260/293.56, 293.58, 260/293.6, 293.62

[56] References Cited
U.S. PATENT DOCUMENTS 3,894,031 7/1975 Hauck et al. .................. 260/293.56

OTHER PUBLICATIONS

Burger "Medicinal Chemistry" 3rd ed. (part II) (1970) pp. 1019–1064.

Primary Examiner—Henry R. Jiles
Assistant Examiner—R. W. Ramsuer
Attorney, Agent, or Firm—Lawrence S. Levinson; Merle J. Smith; Donald J. Barrack

[57] ABSTRACT

Compounds having the formula

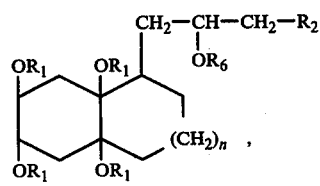

and the pharmaceutically acceptable salts thereof, wherein $n$ is 0, 1 or 2; $R_1$ is alkanoyl; and $R_2$ is

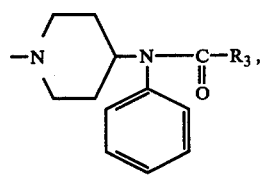

(i)

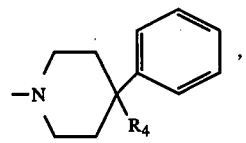

(ii)

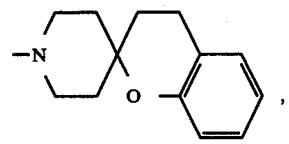

(iii)

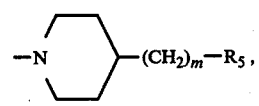

(iv)

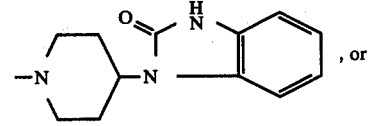

(v)

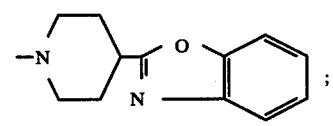

(vi)

$R_3$ is alkyl; $R_4$ is cyano or hydroxy; $R_5$ is hydroxy or alkanoyloxy; $R_6$ is hydrogen or alkanoyl; and $m$ is 2, 3 or 4; have useful hypotensive properties.

11 Claims, No Drawings

SUBSTITUTED PIPERIDINYLPROPANOLS

RELATED APPLICATION

Copending U.S. patent application Ser. No. 784,888, filed Apr. 5, 1977, by Hauck, Fox and Watrous discloses substituted piperazinopropanol hypotensive agents having the formula

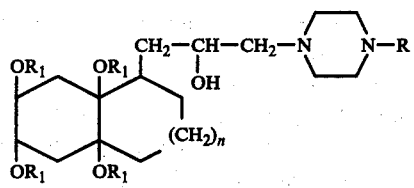

wherein $R_1$ is alkanoyl; R is aryl or pyridinyl; and n is 0, 1 or 2.

Copending U.S. patent application Ser. No. 824,378, filed Aug. 15, 1977, by Hauck, Fox and Watrous, discloses substituted 3,6-dihydro-1(2H)-pyridinylpropanol hypotensive agents having the formula

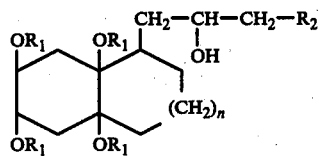

wherein $R_1$ is alkanoyl; $R_2$ is a substituted 3,6-dihydro-1(2H)-pyridinyl derivative; and n is 0, 1 or 2.

BACKGROUND OF THE INVENTION

Cyclitol derivatives having the formula

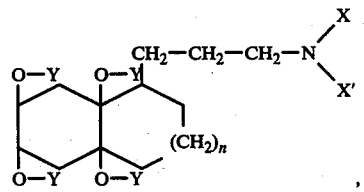

wherein Y is hydrogen or alkanoyl, the group —NXX' is a heterocyclic nitrogen containing group, and n is 0, 1 or 2 are encompassed by the disclosure of U.S. Pat. No. 3,894,031, issued July 8, 1975. Among the heterocyclic groups disclosed are piperazino, (lower alkyl)piperazino, di(lower alkyl)piperazino, (lower alkoxy)piperazino, (hydroxy-lower alkyl)piperazino, (alkanoyloxy-lower alkyl)piperazino, (hydroxy-lower alkoxy-lower alkyl)piperazino, and (carbo-lower alkoxy)piperazino. The treatment of hypertension is one of the utilities for the compounds disclosed by the patent.

Burger, *Medicinal Chemistry*, third edition (part II), John Wiley & Sons, Inc., New York, 1970, chapter 39, "Antihypertensive Agents," pgs. 1019-1064 discloses various classes of antihypertensive agents. Among the classes of compounds disclosed are veratrum alkaloids, the hypotensive activity of which may be largely attributable to the acylation of several hydroxyl functions of an alkamine. Other classes of antihypertensive agents disclosed by Burger include phenoxypropanolamines and phenethanolamines.

BRIEF DESCRIPTION OF THE INVENTION

Compounds having the formula

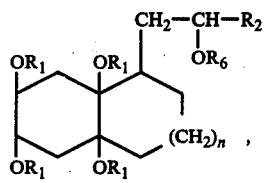

and the pharmaceutically acceptable salts thereof, have hypotensive activity. In formula I, and throughout the specification, the symbols are as defined below.

n is 0, 1 or 2;
$R_1$ is alkanoyl (acetyl is preferred);
$R_2$ is

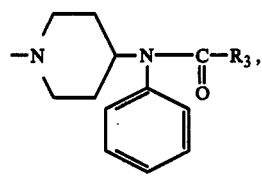

(i)

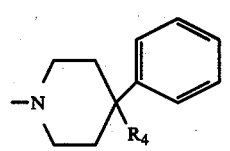

(ii)

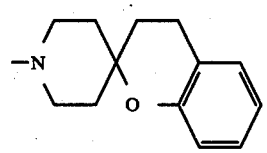

(iii)

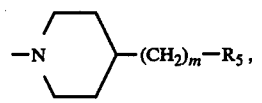

(iv)

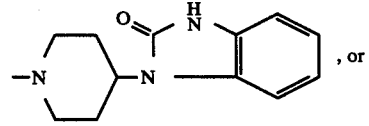

(v)

, or

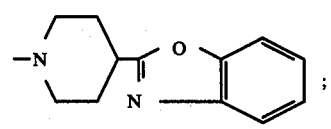

(vi)

;

$R_3$ is alkyl of 1 to 4 carbon atoms;
$R_4$ is cyano or hydroxy;
$R_5$ is hydroxy or alkanoyloxy (acetyloxy is preferred);
$R_6$ is hydrogen or alkanoyl (acetyl is preferred) and m is 2, 3 or 4.

The terms "alkanoyl" and "alkanoyloxy", as used throughout the specification, refer to groups having the formula

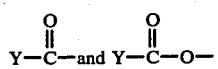

respectively, wherein Y is alkyl having 1 to 6 carbon atoms (i.e., groups having 2 to 7 carbon atoms).

DETAILED DESCRIPTION OF THE INVENTION

The substituted piperidinylpropanols of this invention wherein $R_6$ is hydrogen can be prepared by reacting an oxirane compound having the formula

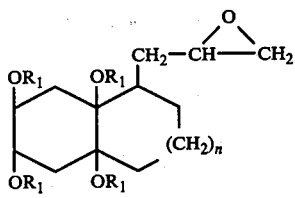

II with a compound having the formula

III

Reaction conditions are not critical, but the reaction proceeds more rapidly when carried out with heating in an organic solvent, or mixture of organic solvents, e.g., a lower alkanol such as ethanol, or an aromatic hydrocarbon such as benzene in combination with a lower alkanol. Those compounds of formula I wherein $R_6$ is alkanoyl can be prepared from the corresponding compound wherein $R_6$ is hydrogen using conventional acylation techniques.

The oxirane compounds of formula II are readily obtained from a corresponding compound having the formula

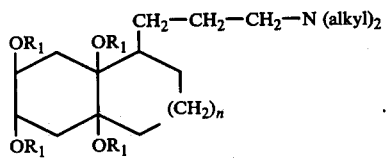

IV

Compounds of formula IV are known; see, for example, U.S. Pat. No. 3,894,031, issued July 8, 1975. Oxidation of a compound of formula IV yields the corresponding N-oxide having the formula

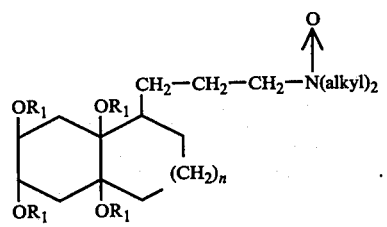

V

Exemplary of oxidizing agents which may be used are the peracids, e.g., m-chloroperbenzoic acid.

Vacuum pyrolysis of an N-oxide of formula V yields an olefin having the formula

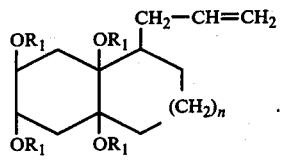

VI

Oxidation of an olefin of formula VI yields the corresponding oxirane compound of formula II. Exemplary of oxidizing agents which may be used are the peracids, e.g., m-chloroperbenzoic acid.

The piperidinyl derivatives of formula II are either known in the art, or can be prepared as described in the examples of this specification.

The compounds of formula I can be converted to their pharmaceutically acceptable acid-addition salts with both organic and inorganic acids using methods well known in the art. Exemplary salts are hydrohalides (e.g., hydrochloride and hydrobromide), nitrate, phosphate, borate, acetate, tartrate, methanesulfonate, benzenesulfonate, toluenesulfonate and the like.

Formula I includes all stereoisomers and mixtures thereof. Particular stereoisomers are prepared by utilizing as the starting material the compound of formula IV with the corresponding stereochemistry. The preferred stereoisomers are those in which the $OR_1$ groups are all axial. Particularly preferred are those compounds having the configuration

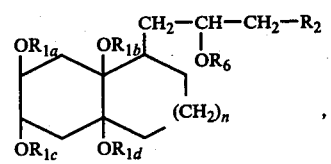

VII wherein the $OR_{1a}$ and $OR_{1c}$ groups are in the trans configuration as are the $OR_{1b}$ and $OR_{1d}$ groups.

The compounds of formula I show hypotensive properties in hypertensive rats and normotensive dogs. The compounds of this invention, and the pharmaceutically acceptable salts thereof, are useful as hypotensive agents in mammals, e.g., domestic animals such as dogs and cats. Daily doses of from 5 to 50 milligrams per kilogram of animal body weight, preferably about 5 to 25 milligrams per kilogram of animal body weight, can be administered orally or parenterally, in single or divided doses.

The compounds of this invention include indan derivatives having the formula

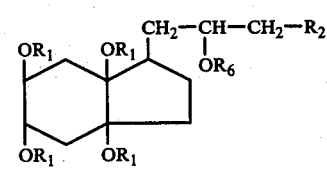

VIII naphthalene derivatives having the formula

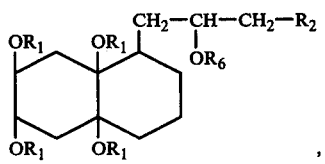

and benzocycloheptane derivatives having the formula

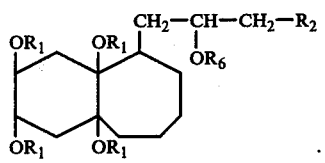

the naphthalene derivatives of formula IX are preferred.

The following examples are specific embodiments of this invention.

EXAMPLE 1

3,4a,5-cis-Decahydro-5-[2-hydroxy-3-[4-[(1-oxo-propyl)phenylamino]-1-piperidinyl]propyl]-2,3;4a,8a-transnaphthalenetetrol, tetraacetate ester 3,4a,5-cis-Decahydro-5-(oxiranylmethyl)-2,3;4a,8a-trans-naphthalenetetrol, tetraacetate ester (3.37g, see copending U.S. patent application Ser. No. 784,888, filed Apr. 5, 1977) is dissolved in 50ml of absolute ethanol and 20ml of benzene. To this solution is added 1.75g of N-phenyl-N-4-piperidinylpropanamide and the resulting solution is heated to 55° C. ± 50 for 16 hours. The solvent is stripped off in vacuo and the resulting gum is taken up in ether and left for about 16 hours to crystallize, yielding (after drying) 3.9g of powder. Crystallization of the powder from ethyl acetate-hexane yielding 3.1g of powder, melting point 153°–160° C.

EXAMPLE 2

1-[2-Hydroxy-3-[cis-1,7,8a-4a,6,7,8a-tetrakis(acetyloxy)decahydro-1-naphthalenyl]propyl]-4-phenyl-4-piperidinecarbonitrile A solution of 1.0g of 4-cyano-4-phenylpiperidine and 2.5g of 3,4a,5-cis-decahydro-5-(oxiranylmethyl)-2,3;4a,-8a-trans-naphthalenetetrol, tetraacetate ester in 20ml benzene-50ml ethanol is stirred at 55°–57° C. for about 16 hours under a drying tube. The solution is evaporated in vacuo to give 3.3g of oil. Chromatography on 80g of neutral alumina III gives 1.06 of epoxide eluted with 600 ml of 20–25% ethyl acetate in hexane, and 1.4g of the desired product eluted with 750ml of 40–45% ethyl acetate in hexane. Crystallization of this latter material from ethyl acetate hexane gives two crops of solid product. These are combined and dried in vacuo to yield 0.97g of the title compound, melting point 165°–174° C.

EXAMPLE 3

3,4a-5-cis-Decahydro-5-[2-hydroxy-3-(4-hydroxy-4-phenyl-1-piperidinyl)propyl]-2,3;4a,8a-trans-naphthalenetetrol, tetraacetate ester A solution of 3.0g of 3,4a,5-cis-decahydro-5-(oxiranylmethyl)-2,3;4a,8a-trans-naphthalenetetrol, tetraacetate ester and 1.25g of 4-hydroxy-4-phenyl piperidine in 50ml of absolute ethanol-20ml benzene is stirred at 57° C. for about 16 hours. Crystallization from 2:1 ethyl acetate-hexane gives 3.5g of solid. Recrystallization from ethyl acetate-hexane (20:5) gives 2.11g of the title compound, melting point 138°–142° C.

EXAMPLE 4

3,4a,5-cis-Decahydro-5-[2-hydroxy-3-(3,4-dihydrospiro[2H-1-benzopyran-2,4'-piperidin]-1-yl)propyl]-2,3;4a,8a-trans-naphthalenetetrol, tetraacetate ester (A)

3,4-Dihydro-1'-(phenylmethyl)spiro[2H-1-benzopyran-2,4'-piperidine], hydrochloride (1:1)

4-(o-Methoxyphenethyl)pyridine (40.5 g) and benzylbromide (36.0 g) are heated on a steam cone in 250 ml of acetonitrile for 6 hours. After cooling the reaction mixture is concentrated in vacuo. Addition of ethyl acetate causes crystallization. The product is filtered, washed with ether and dried over potassium hydroxide. The yield of a hydroscopic quaternary is 68.4 g, melting point 114°–124° C.

The above quaternary (60.6 g) is dissolved in 600 ml of 1:1 methanol-water and 10 g of sodium borohydride is added portionwise at 35°–40° C. After addition, the solution is allowed to stand for about 16 hours. It is then concentrated to about 400 ml and diluted with 300 ml of water. The product is extracted with two 300 ml portions of chloroform. The chloroform is dried, filtered and concentrated in vacuo. The hydrochloride salt is prepared in isopropanol-hydrogen chloride. After concentrating in vacuo, ethyl acetate is added to the residue. The hydrochloride salt crystallizes over a 16-hour period and is filtered to yield 54 g of product, melting point 122°–128° C.

The above product (54.0 g) is dissolved in 250 ml of 48% hydrogen bromide. It is then heated at reflux for 6 hours and concentrated in vacuo. The residue is made strongly basic with 10% sodium hydroxide and the product is extracted with chloroform. The chloroform is dried, filtered and concentrated in vacuo. This free base is dissolved in ethyl acetate, and hydrogen chloride in isopropanol is added until strongly acidic. The product is filtered to yield 39.4 g. Two grams are recrystallized from acetonitrile to give the analytical sample, melting point 243°–245° C.

(B) 3,4-Dihydrospiro[2H-1-benzopyran-2,4'-piperidine]

3,4-Dihydro-1'-(phenylmethyl)spiro[2H-1-benzopyran-2,4'-piperidine] (25.7 g) is dissolved in 250 ml of anhydrous toluene. The reaction mixture is cooled to 5° C. and trichloroethyl chloroformate is added dropwise. The solution is refluxed for 5 hours and allowed to stand at room temperature for about 16 hours. It is then washed sequentially with 100 ml of 10% sodium hydroxide, 100 ml of water, 100 ml of 10% hydrochloric acid and finally with 200 ml of water. The toluene is dried, filtered and concentrated in vacuo to yield 32.0 g of product.

The above material is dissolved in 300 ml of glacial acetic acid. Zinc dust (30 g) is added portionwise over a 30-minute period at 20° C. The reaction mixture is stirred at room temperature for about 16 hours, filtered and concentrated in vacuo. The residue is heated on a steam cone for 15 minutes in 200 ml of 10% sodium hydroxide. Product is extracted with chloroform. The chloroform is dried, filtered and concentrated in vacuo to yield 17.8 g of crude secondary amine. Its hydrochloride salt was prepared in isopropanol-hydrogen chloride. After crystallizing for about 16 hours, the product is filtered to yield 11.1 g of the hydrochloride salt of the title compound, melting point 238°–240° C.

(C)

3,4a,5-cis-Decahydro-5-[2-hydroxy-3-(3,4-dihydrospiro-[2H-1-benzopyran-2,4-piperidin]-1-yl)propyl]-2,3;4a,8a-trans-naphthalenetetrol, tetraacetate ester An amount of 1.7 g of 3,4-dihydrospiro[2H-1-benzopyran-2,4'-piperidine] is added to a solution of 3.55 g of 3,4a,5-cis-decahydro-5-(oxiranylmethyl)-2,3;4a,8a-trans-naphthalenetetrol, tetraacetate ester in 50:20 ml of ethanol-benzene. The solution is stirred for about 16 hours at 55° C. and then evaporated in vacuo. The residue is crystallized over 3 days from 2:1 ether-hexane to give 3.6 g of solid. Recrystallization from ethyl acetate-hexane gives 2.3 g of the title compound (thin-layer chromatography on alumina in ethyl acetate developed in iodine indicates the title compound to be the main isomer of two isomers), melting point 135°–152° C.

EXAMPLE 5

3,4a,5-cis-Decahydro-5-[2-hydroxy-3-[4-(2-hydroxyethyl)-1-piperidinyl]propyl]-2,3;4a,8a-trans-naphthalenetetrol, tetraacetate ester A solution of 2.5 g of 3,4a,5-cis-decahydro-5-(oxiranylmethyl)-2,3;4a,8a-trans-naphthalenetetrol, tetraacetate ester and 0.75 g of 4-ethanolpiperidine in 50 ml of absolute ethanol and 20 ml of benzene is stirred at 55° C. for 18 hours. The solvents are removed in vacuo and the residue is concentrated in vacuo several times with benzene to give a foam-like product. Crystallization from ether gives 2.55 g and then 0.5 g of solid product. Recrystallization of the 3 g of solid from 2:1 ethyl acetate-hexane gives 2.0 g of the title compound, melting point 112°–120° C.

EXAMPLE 6

3,4a,5-cis-5-[2-(Acetyloxy)-3-[4-[2-(acetyloxy)ethyl]-1-piperidinyl]propyl]-decahydro-2,3;4a,8a-trans-naphthalenetetrol, tetraacetate ester A mixture of 5 ml of acetic anhydride and 1.25 g of 3,4a,5-cis-decahydro-5-[2-hydroxy-3-[4-(2-hydroxyethyl)-1-piperidinyl]propyl]-2,3;4a,8a-trans-naphthalenetetrol, tetraacetate ester (see Example 5) in 25 ml of dry pyridine is stirred at room temperature for about 16 hours. The solution is evaporated in vacuo. The residue is partitioned between ether and a saturated aqueous sodium bicarbonate solution. The aqueous layer is re-extracted with ether, and the ether extracts are combined, dried and evaporated in vacuo yielding 1.3 g of product. Recrystallization from 1:9 ethyl acetate-hexane yields 1.22 g of the title compound, melting point 125°–144° C.

EXAMPLE 7

3,4a,5-cis-5-[3-(2,3-Dihydro-2-oxo-1H-benzimidazol-1-yl)-1-piperidinyl]-2-hydroxypropyl]decahydro-2,3;4a,8a-trans-naphthalenetetrol, tetraacetate ester An amount of 1.5 g of 3,4a,5-cis-decahydro-5-(oxiranylmethyl)-2,3;4a,8a-trans-naphthalenetetrol, tetraacetate ester is dissolved in 20 ml of benzene and 50 ml of absolute ethanol and maintained at 50° C.±5° with a water bath. To this is added 0.73 g of 4-(2-keto-1-benzimidazolinyl)piperidine and stirring is continued for 36 hours. Solvent is stripped in vacuo, and the product is crystallized from ethyl acetatehexane to yield 1.67 g of material, melting point 137°–144° C.

EXAMPLE 8

3,4a,5-cis-5-[3-[4-(2-Benzoxazolyl)-1-piperidinyl]-2-hydroxypropyl]-decahydro-2,3;4a,8a-naphthalenetetrol, tetraacetate ester (A) 2-(4-Piperidinyl)benzoxazole A solution of 1.71 g of benzyl bromide in 10 ml of acetonitrile is added to a solution of 1.96 g of 2-(4-pyridinyl)benzoxazole in 25 ml of hot acetonitrile. After 10 minutes the product begins to crystallize out of solution. The mixture is heated on the steam bath for 2 hours and then diluted with ether and filtered. The crude solid is dissolved in 50 ml of 1:1 methanol-water and treated portionwise with 2 g of sodium borohydride. The mixture is diluted with water and 2.4 g of the solid product is collected. The 2.4 g of solid is dissolved in 150 ml of ethanol, 2 g of 5% paladium on carbon is added, and the mixture is placed on the Parr hydrogenator under 50 psi hydrogen. The mixture is filtered, and the filtrate evaporated in vacuo to give 1.4 g of the title compound.

(B)

3,4a,5-cis-5-[3-[4-(2-Benzoxazolyl)-1-piperidinyl]-2-hydroxypropyl]decahydro-2,3;4a,8a-trans-naphthalenetetrol, tetraacetate ester A solution of 3.6 g of 3,4a,5-cis-decahydro-5-(oxiranylmethyl)-2,3;4a,8a-trans-naphthalenetetrol, tetraacetate ester and 1.4 g of the 2-(4-piperidinyl)benzoxazole in 20 ml of benzene and 50 ml of absolute ethanol is stirred for 7.5 hours at 55° C. and then for about 16 hours at room temperature under nitrogen. The solution is evaporated in vacuo and the residue dissolved in hot ethyl acetate (30–40 ml), diluted with hexane (30 ml) and crystallized on standing to give 3.14 g of solid. The solid is dissolved in hot ethyl acetate (50 ml), treated with Darco, filtered, and diluted with hexane (20 ml). The solution crystallizes to give 2.02 g of the title compound, melting point 195°–205° C.

EXAMPLES 9–10

Following the procedure of Example 1, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column 1 | Column II |
| --- | --- |
| 9) 3a,5-cis-3a,7a;5,6-trans-hexahydro-1-(oxiranylmethyl)-1H-indene-3a,5,6,-7a-tetrol, tetraacetate ester (see U.S. Pat. Application Ser. No. 784,888, filed April 5, 1977) | 3a,5-cis-3a,7a;5,6-trans-hexahydro-1-[2-hydroxy-3-[4-[(1-oxopropyl)phenylamino]-1-piperidinyl]-propyl]-1H-indene-3a,5,6,-7a-tetrol, tetraacetate ester |
| 10) 3,4a,5-cis-hexahydro-5-(oxiranylmethyl)-2,3;4a,-9a-trans-benzocycloheptane-tetrol, tetraacetate ester (see U.S. Pat. Application Ser. No. 784,888, filed April 5, 1977) | 3,4a,5-cis-hexahydro-5-[2-hydroxy-3-[4-[(1-oxopropyl)phenylamino]-1-piperidinyl]propyl]-2,3;-4a,9a-trans-benzocycloheptanetetrol, tetraacetate ester |

EXAMPLES 11–12

Following the procedure of Example 2, but substituting the compound listed in column I for 3,4a,5-cisdecahydro-5-(oxiranylmethyl)-2,3;4a,8a-trans-naphthalenetetrol, tetraacetate ester yields the compound listed in column II.

| Column I | Column II |
|---|---|
| 11) 3a,5-cis-3a,7a;5,6-trans-hexahydro-1-(oxiranylmethyl)-1H-indene-3a,5,6,7a-tetrol, tetraacetate ester | 1-[2-hydroxy-3-[cis-3a,5-3a,5,6,7a-tetrakis(acetyloxy)hexahydro-1H-inden-1-yl]propyl]-4-phenyl-4-piperidinecarbonitrile. |
| 12) 3,4a,5-cis-hexahydro-5-(oxiranylmethyl)-2,3;4a,9a-trans-benzocycloheptanetetrol, tetraacetate ester | 1-[2-hydroxy-3-[cis-1,8,9a-2,3,4a,9a-tetrakis(acetyloxy)hexahydro-1-benzocycloheptanyl]propyl]-4-phenyl-4-piperidinecarbonitrile |

EXAMPLES 13–14

Following the procedure of Example 3, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 13) 3a,5-cis-3a,7a;5,6-trans-hexahydro-1-(oxiranylmethyl)-1H-indene-3a,5,6,7a,tetrol, tetraacetate ester | 3a,5-cis-3a,7a;5,6-trans-hexahydro-1-[2-hydroxy-3-(4-hydroxy-4-phenyl-1-piperidinyl)propyl]-1H-indene-3a,5,6,7a-tetrol, tetraacetate ester |
| 14) 3,4a,5-cis-hexahydro-5-(oxiranylmethyl)-2,3;4a,-9a-trans-benzocycloheptanetetrol, tetraacetate ester | 3,4a,5-cis-hexahydro-5-[2-hydroxy-3-(4-hydroxy-4-phenyl-1-piperidinyl)-propyl]-2,3;4a,9a-trans-benzocycloheptanetetrol, tetraacetate ester |

EXAMPLES 15–16

Following the procedure of Example 4, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 15) 3a,5-cis-3a,7a;5,6-trans-hexahydro-1-(oxiranylmethyl)-1H-indene-3a,5,6,-7a-tetrol, tetraacetate ester | 3a,5-cis-3a,7a;5,6-trans-hexahydro-1-[2-hydroxy-3-(3,4-dihydrospiro[2H-1-benzopyran-2,4'-piperidin]-1-yl)propyl]-1H-indene-3a,5,6,7a-tetrol, tetraacetate ester |
| 16) 3,4a,5-cis-hexahydro-5-(oxiranylmethyl)-2,3;4a,-9a-trans-benzocycloheptanetetrol, tetraacetate ester | 3,4a,5-cis-hexahydro-5-[2-hydroxy-3-(3,4-dihydrospiro[2H-benzopyran-2,4'-piperidin]-1-yl)propyl]-2,3;4a,9a-trans-benzocycloheptanetetrol, tetraacetate ester |

EXAMPLES 17–18

Following the procedure of Example 5, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 17) 3a,5-cis-3a,7a;5,6-trans-hexahydro-1-(oxiranylmethyl)-1H-indene-3a,5,6,7a,tetrol, tetraacetate ester | 3a,5-cis-3a,7a;5,6-trans-hexahydro-1-[2-hydroxy-3-[4-(2-hydroxyethyl)-1-piperidinyl]propyl]-1H-indene-3a,5,6,7a-tetrol, tetraacetate ester |
| 18) 3,4a,5-cis-hexahydro-5-(oxiranylmethyl)-2,3;4a,9a-trans-benzocycloheptanetetrol, tetraacetate ester | 3,4a,5-cis-hexahydro-5-[2-hydroxy-3-[4-(2-hydroxyethyl)-1-piperidinyl]propyl]-2,3;4a,9a-trans-benzocycloheptanetetrol, tetraacetate ester |

EXAMPLES 19–20

Following the procedure of Examples 5 and 6, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 19) 3a,5-cis-3a,7a;5,6-trans-hexahydro-1-(oxiranylmethyl)-1H-indene-3a,5,6,-7a-tetrol, tetraacetate ester | 3a,5-cis-3a,7a;5,6-trans-hexahydro-1-[2-(acetyloxy)-3-[4-[2-(acetyloxy)ethyl]-1-piperidinyl]propyl]-1H-indene-3a,5,6,7a-tetrol, tetraacetate ester |
| 20) 3,4a,5-cis-hexahydro-5-(oxiranylmethyl)-2,3;4a,9a-trans-benzocycloheptanetetrol, tetraacetate ester | 3,4a,5-cis-hexahydro-5-[2-(acetyloxy)-3-[4-[2-(acetyloxy)ethyl]-1-piperidinyl]propyl]-2,3;4a,9a-trans-benzocycloheptanetetrol, tetraacetate ester |

EXAMPLES 21–22

Following the procedure of Example 7, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 21) 3a,5-cis-3a,7a;5,6-trans-hexahydro-1-(oxiranylmethyl)-1H-indene-3a,5,6,-7a-tetrol, tetraacetate ester | 3a,5-cis-3a,7a;5,6-trans-hexahydro-1-[3-(2,3-dihydro-2-oxo-1H-benzimidazol-1-yl)-1-piperidinyl]-2-hydroxypropyl]-1H-indene-3a,5,6,7a-tetrol, tetraacetate ester |
| 22) 3,4a,5-cis-hexahydro-5-(oxiranylmethyl)-2,3;4a,9a-trans-benzocycloheptanetetrol, tetraracetate ester | 3,4a,5-cis-hexahydro-5-[3-(2,3-dihydro-2-oxo-1H-benzimidazol-1-yl)-1-piperidinyl]-2-hydroxypropyl]-2,3;4a,9a-trans-benzocycloheptanetetrol, tetraacetate ester |

EXAMPLES 23–24

Following the procedure of Example 8, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 23) 3a,5-cis-3a,7a;5,6-trans-hexahydro-1-(oxiranylmethyl)-1H-indene-3a,5,6,-7a-tetrol, tetraacetate ester | 3a,5-cis-3a,7a;5,6-trans-hexahydro-1-[3-[4-(2-benzoxazolyl)-1-piperidinyl]-2-hydroxypropyl]-1H-indene-3a,5,6,7a-tetrol, tetraacetate ester |
| 24) 3,4a,5-cis-hexahydro-5-(oxiranylmethyl)-2,3;4a,9a-trans-benzocycloheptane- | 3,4a,5-cis-hexahydro-5-[3-[4-(2-benzoxazolyl)-1-piperidinyl]-2-hydroxy- |

-continued

| Column I | Column II |
|---|---|
| tetrol, tetraacetate ester | propyl]-2,3;4a,9a-trans-benzocycloheptanetetrol, tetraacetate ester |

What is claimed is:

1. A compound having the formula

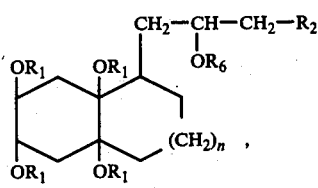

or a pharmaceutically acceptable salt thereof, wherein $n$ is 0, 1 or 2; $R_1$ is alkanoyl having 2 to 7 carbon atoms; and $R_2$ is (i) 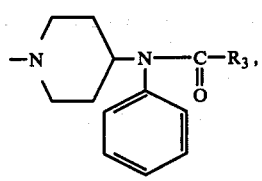

(ii) 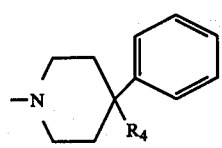

(iii) 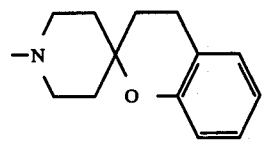

(iv) 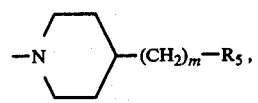

(v) 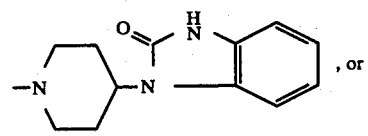, or (vi) 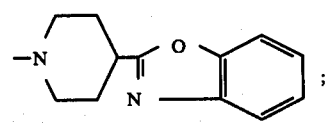;

$R_3$ is alkyl of 1 to 4 carbon atoms; $R_4$ is cyano or hydroxy; $R_5$ is hydroxy or alkanoyloxy of 2 to 7 carbon atoms; $R_6$ is hydrogen or alkanoyl of 2 to 7 carbon atoms and $m$ is 2, 3 or 4.

2. A compound in accordance with claim 1 wherein $n$ is 1 and $R_6$ is hydrogen.

3. A compound in accordance with claim 2 wherein $R_1$ is acetyl.

4. A compound in accordance with claim 3 wherein $R_2$ is

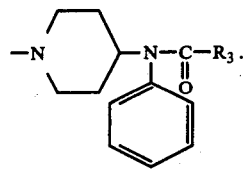

5. A compound in accordance with claim 3 wherein $R_3$ is

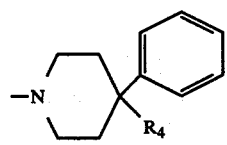

6. A compound in accordance with claim 5 wherein $R_4$ is cyano.

7. A compound in accordance with claim 5 wherein $R_4$ is hydroxy.

8. A compound in accordance with claim 3 wherein $R_2$ is

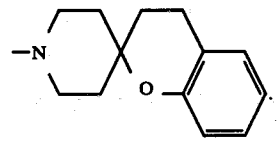

9. A compound in accordance with claim 3 wherein $R_2$ is

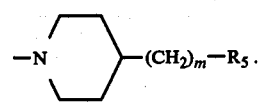

10. A compound in accordance with claim 3 wherein $R_2$ is

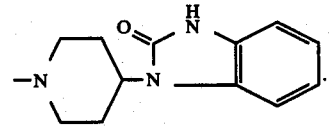

11. A compound in accordance with claim 3 wherein $R_2$ is

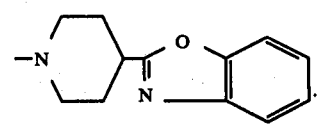

* * * * *

UNITED STATES PATENT AND TRADEMARK OFFICE
CERTIFICATE OF CORRECTION

PATENT NO. : 4,127,579
DATED : November 28, 1978
INVENTOR(S) : Frederic P. Hauck, et al.

It is certified that error appears in the above-identified patent and that said Letters Patent are hereby corrected as shown below:

Column 2, lines 5-13, the structure should read:

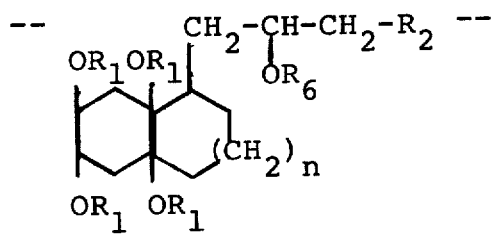

Signed and Sealed this

Tenth Day of July 1979

[SEAL]

Attest:

*Attesting Officer*

LUTRELLE F. PARKER
*Acting Commissioner of Patents and Trademarks*